US005846552A

United States Patent [19]
Mahe et al.

[11] Patent Number: 5,846,552
[45] Date of Patent: Dec. 8, 1998

[54] USE OF 2,4-DIAMINOPYRIMIDINE 3-OXIDE OR A SALT THEREOF FOR TREATING COLLAGEN MATURATION AND STRUCTURING DISORDERS

[75] Inventors: Yann Mahe, Morsang-sur-orge; Lionel Breton, Versailles; Jean-Baptiste Galey, Aulnay-sous-bois; Bruno Bernard, Neuilly-sur-seine, all of France

[73] Assignee: L'Oreal, Paris, France

[21] Appl. No.: 809,950

[22] PCT Filed: Sep. 19, 1995

[86] PCT No.: PCT/FR95/01197

§ 371 Date: Jun. 9, 1997

§ 102(e) Date: Jun. 9, 1997

[87] PCT Pub. No.: WO96/09048

PCT Pub. Date: Mar. 28, 1996

[30] Foreign Application Priority Data

Sep. 19, 1994 [FR] France ................................. 94 11133

[51] Int. Cl.[6] ............................................. A61K 6/00
[52] U.S. Cl. ........................... 424/401; 514/272; 424/449
[58] Field of Search ................................. 424/401, 449; 514/272

[56] References Cited

U.S. PATENT DOCUMENTS

| 4,421,914 | 12/1983 | Okamura | 544/278 |
| 5,091,522 | 2/1992 | Phillippe | 536/17.2 |

FOREIGN PATENT DOCUMENTS

| 0548883 | 12/1992 | European Pat. Off. . |
| 92 01437 | 2/1992 | WIPO . |

OTHER PUBLICATIONS

Handa et al: "Minoxidil inhibits ocular cell proliferation and lysyl hydroxlase activity", Invest. Ophthalmol. Visual Sci., vol. 34, No. 3, 1993. pp. 567–575.

Handa et al: "Inhibition of cultured human RPE cell proliferation and lysyl hydroxlase activity by hydrogen derivatives of minoxdil.", Invest. Ophthamol. Visual Sic., vol. 35, No. 2, 1994, pp. 463–469.

*Primary Examiner*—D. Gabrielle Brouillette

[57] ABSTRACT

The Use of 2,4-diamino pyrimidine 3-oxide or a physiologically acceptable salt thereof as the active substance for the preparation of a therapeutical composition is disclosed. Said therapeutical composition is useful for treating collagen maturation and structuring disorders.

11 Claims, 1 Drawing Sheet

USE OF 2,4-DIAMINOPYRIMIDINE 3-OXIDE OR A SALT THEREOF FOR TREATING COLLAGEN MATURATION AND STRUCTURING DISORDERS

This application is the national phase of international application PCT/FR95/01197 filed Sep. 19, 1995 which designated the U.S.

The present invention relates to the use as an active substance of 2,4-diaminopyrimidine 3-oxide or a salt thereof for the preparation of a therapeutic composition for pharmaceutical or veterinary application intended for the treatment of collagen maturation and structuring disorders.

To obtain bundles of native procollagen requires the hydroxylation of a certain number of prolyl and lysyl residues of preprocollagen within the rough endoplasmic reticulum, followed by the glycosylation of the hydroxylysyl residues in the Golgi apparatus. This maturation of collagen has been the subject of numerous studies.

Thus, minoxidil, namely 2,4-diamino-6-piperidino-pyrimidine 3-oxide, already described and used in the treatment of some types of hypertension and in the treatment of androgenic alopecia, has been the subject of numerous studies as a specific inhibitor of lysyl hydroxylase, an enzyme participating in the maturation of collagen.

In this connection, the studies of Murad et al., published in Arch. of Biochem. Biophys., Vol. 292, No. 1, pp. 234–238 (1992) and Vol. 308, No. 1, pp. 42–47 (1994), have, in effect, enabled it to be shown that the ability to inhibit lysyl hydroxylase necessitated the presence of a tertiary amine group located at the para position with respect to the N-oxide function of the 2,4-diamino-pyrimidine ring, and that this group preferably needed to be a piperidine group as in minoxidil.

In point of fact, it has now been established, surprisingly and quite unexpectedly, that 2,4-diamino-pyrimidine 3-oxide or 2,4-DPO (hereinafter), although it does not contain a tertiary amine group at the para position with respect to the N-oxide function of the 2,4-diaminopyrimidine ring, enables lysyl hydroxylase to be specifically inhibited.

This compound has already been described in WO 92/01437 as an active agent intended for the cosmetic treatment, by topical application, of hair loss. However, contrary to minoxidil, 2,4-DPO does not possess any antihypertensive effect, and is hence especially satisfactory from the standpoint of safety while having an inhibitory activity with respect to lysyl hydroxylase which is equal to or even greater than that of minoxidil.

Figure 1A:
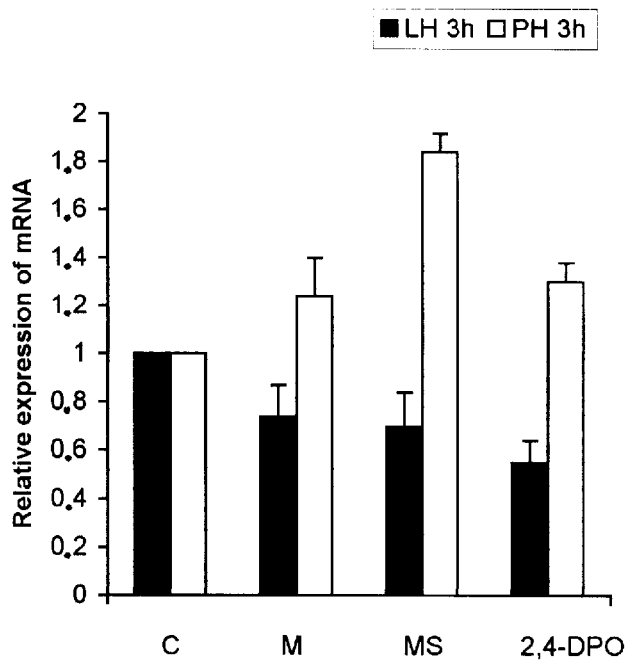
FIG. 1A demonstrates Relative Expression of mRNA at 3 h for C: Control, M: minoxidil, MS: Minoxidil sulphate, 2,4-DPO: 2,4-Diaminopyrimidine 3-oxide, LH: Lysylhydroxylase, PH: propylhydroxylase.

The subject of the present invention is hence the use as an active substance of 2,4-DPO or a salt thereof for the preparation of a therapeutic composition for pharmaceutical or veterinary application intended for the treatment of collagen maturation disorders in man or animals.

Hereinafter, the expression "2,4-DPO" will mean not only 2,4-DPO itself but also a salt thereof as defined below.

Collagen maturation disorder should be understood, according to the invention, to mean any undesired accumulation of collagen, and in particular any structural disorder of the collagen matrix of the cutaneous tissue or bulbar conjunctiva; these disorders may be of spontaneous, traumatic or postoperative origin. Among these disorders, vitreoretinopathy, systemic scleroderma, ultraviolet-induced cutaneous thickening and cicatricial keloid may be mentioned in particular.

The use of 2,4-DPO according to the invention hence makes it possible to obtain, in particular, an aesthetic improvement in the patient undergoing treatment.

While, according to the invention, the treatment may be curative, it is nonetheless preferably used preventively, that is to say during the period in which structuring, and consequently the accumulation of collagen, takes place, this occurring, in particular, during the period of cicatrization.

2,4-DPO may be used for the preparation of a therapeutic composition presented in a form which can be administered topically, transdermally or intradermally.

Physiologically acceptable salts should be understood, according to the invention, to mean addition salts with an acid such as those with sulphuric, hydrochloric, phosphoric, acetic, benzoic, salicylic, glycolic, aceturic, succinic, nicotinic, tartaric, maleic, methanesulphonic, picric and lactic acids.

When the therapeutic composition is presented in a form which can be administered topically, the proportion of 2,4-DPO is generally between 0.0001 and 5% by weight, and preferably between 0.01 and 2% by weight, relative to the total weight of the composition.

The nature of the vehicle can vary widely, but the latter is preferably a physiologically acceptable medium for topical application, which is, of course, compatible with the active substance.

The 2,4-DPO in this medium can be either in the dissolved state or in the dispersed state, in particular in micronized form.

The physiologically acceptable medium can consist of water or a mixture of water and a solvent or a mixture of solvents. Among solvents which can be used, $C_1$–$C_4$ lower alcohols such as ethanol, isopropanol and tert-butanol, alkylene glycols and alkylene glycol and dialkylene glycol alkyl ethers such as ethylene glycol monoethyl ether, propylene glycol monomethyl ether and diethylene glycol monoethyl ether may be mentioned in particular. These compositions intended for topical application may also contain at least one conventional additive or an active principle.

Among these latter, UV-A and UV-B screening agents such as methoxycinnamates and benzophenone derivatives, antioxidants and/or free radical scavengers such as DMSO, α-tocopherol, BHA, BHT and superoxide dismutase, hydrating agents such as urea, glycerol, lactic acid, hydroxy acids, thiamorpholinone and its derivatives and derivatives of pyrrolidonecarboxylic acid, in particular its sodium and potassium salts, steroidal and non-steroidal anti-inflammatory agents such as hydrocortisone, β-methasone, dexamethasone, acetylsalicylic acid, indomethacin, ibuprofen, vitamin D or niflumic acid, and antibacterials such as those belonging to the macrolide, pyranoside and tetracycline groups, such as erythromycin, may be mentioned in particular.

These compositions may also contain preservatives, stabilizing agents, pH regulating agents, osmotic pressure modifiers and emulsifying agents.

These compositions intended for topical application, based on 2,4-DPO, may be presented in various forms, such as, for example, in the form of lotions, gels, foams, vesicular dispersions, sprays or aerosol foams.

These compositions may also be presented in the form of gelled or thickened compositions. Among gelled compositions, special mention may be made of essentially aqueous compositions gelled with heterobiopolysaccharides such as xanthan gum, scleroglucans or cellulose derivatives, and especially cellulose ethers, or aqueous-alcoholic compositions gelled with polyhydroxyethyl acrylates or methacrylates. Among thickened aqueous compositions, those obtained, in particular, using a polyacrylic acid crosslinked with a polyfunctional agent, such as the ones marketed under the names "Carbopol®" by the company Goodrich, may be mentioned. It is of course possible, however, to use as thickening agent any agent customarily employed in pharmacy or in dermopharmacy.

When administered topically, 2,4-DPO is generally applied to the parts of the body to be treated in the proportion of 0.0001 to 5 mg/kg/day, and preferably 0.001 to 1 mg/kg/day. The treatment is generally continued throughout the period during which the accumulation of collagen takes place, and may, where appropriate, be continued for 90 days after this period.

It is also possible, according to the invention, to use 2,4-DPO for the preparation of therapeutic compositions intended for transdermal administration.

The proportion of 2,4-DPO is then generally between 0.001 and 5%, and preferably between 0.01 and 2%, relative to the total weight of the composition.

The excipient used in these compositions is generally chosen from vinyl polymers or copolymers, with the addition of a penetration promoter where appropriate.

The compositions intended for transdermal application may be administered, in particular, using a self-adhesive system that adheres to the skin and provides for the continuous passage, for at least 24 hours, of a controlled amount of active substance through the skin into the blood stream.

Among these systems, those described in Application FR 88/11685 (2,635,979) as well as those marketed by the company Tilderm may be mentioned in particular.

2,4-DPO may also be used for the preparation of therapeutic compositions intended for intradermal administration.

The proportion of 2,4-DPO is then generally between 0.0001 and 5% by weight, and preferably between 0.01 and 1% by weight, relative to the total weight of the composition.

2,4-DPO is then in soluble form in a physiologically acceptable vehicle such as physiological saline.

The compositions intended for intradermal administration may comprise, in addition, various therapeutic agents such as, for example, antibacterial agents, antioxidants and steroidal and non-steroidal anti-inflammatories.

2,4-DPO is generally administered intradermally on the basis of a dose not exceeding 5 mg/kg/day, and preferably between 0.0001 and 1 mg/kg/day. The treatment is generally applied throughout the period during which the accumulation of collagen takes place, and may, where appropriate, be continued for 30 days after this period.

Although reference has been made above more especially to compositions intended for a pharmaceutical application, it is self-evident that these compositions may be formulated in a form more suitable for a veterinary application, in particular in the treatment of members of the family Equidae such as horses.

Irrespective of the mode of administration or the application for which they are intended, the compositions according to the invention are prepared according to known methods.

The results of studies demonstrating the efficacy of 2,4-DPO, as well as various examples of therapeutic compositions, will now be given by way of illustration.

I—Study of the inhibition of the expression of mRNAs coding for lysyl hydroxylase (LH)

From a culture of fibroblasts originating from external connective tissue sheaths of human hair at the firth subculturing, $2 \times 10^5$ fibroblasts are inoculated into Petri dishes 60 mm in diameter containing Dulbecco's modified Eagle's culture medium supplemented with 2 mM L-glutamine, 1 mM sodium pyruvate, 100 units/ml of penicillin G, 100 µg/ml of steptomycin S, 250 mg/ml of amphotericin and 10% of foetal calf serum marketed by the Company Gibco BRL.

After 24 hours of culture at 37° C. in an incubator in a 95% air/5% $CO_2$ atmosphere, the medium is replaced by a similar medium not, however, containing foetal calf serum. The cells are then incubated at 37° C. for 3 hours (FIG. 1A) or 18 hours (FIG. 1B) in the presence of 5 mM minoxidil, 5 mM 2,4-DPO or 5 mM minoxidil sulphate.

According to the method described in "Short protocols in molecular biology, Harvard Medical School, J. Wiley and sons publisher, 1992", the total RNA is extracted from each of the cell preparations and then quantified by UV spectrophotometric measurement at 280 nm.

To permit the analysis of the expression of the mRNAs, amplification of the latter is performed by a polymerization chain reaction (PCR).

From 2 µg of total RNA obtained above for each cell preparation, the complementary DNA is synthesized in vitro using a reverse transcription kit marketed under the name "First Strand C-DNA Synthesis kit" by the company Pharmacia LKB Biotechnology AB. An aliquot fraction of the complementary DNA obtained above is then amplified by the actual PCR method in the presence of the following specific primers for lysyl hydroxylase (LH) and prolyl hydroxylase (PH):

LH sense primer: 5'GAAATGGGCCATGTGAGAGCG3'

LH antisense primer: 5'TGTGGATGACAATAGTCG-GCACG3'

PH sense primer: 5'GTGGATGGAACAAGC-CCTAAGGC3'

PH antisense primer: 5'CCTCCCCACGGCACAGCATTTCG3', for a final volume of 50 µl.

20 µl of the mixture obtained after PCR are applied to a 2% agarose electrophoresis gel in the presence of 0.5 µg/ml of ethidium bromide and the 1× Tris-acetate EDTA (TAE) electrophoresis buffer.

After migration for 1 hour in an electric field of 100 V, the intensity of the bands corresponding to the mRNAs coding for lysyl hydroxylase and prolyl hydroxylase, respectively, is analysed and quantified by means of an image analyzer and the software marketed under the name "Bioprofil®" by the company Vilbert Lourmat.

According to the same procedure as described above, the levels of relative expression of the mRNAs coding for lysyl hydroxylase and for prolyl hydroxylase after 3 hours and 18 hours of culture of fibroblasts in the absence of any treatment are also measured.

Figure 1B:
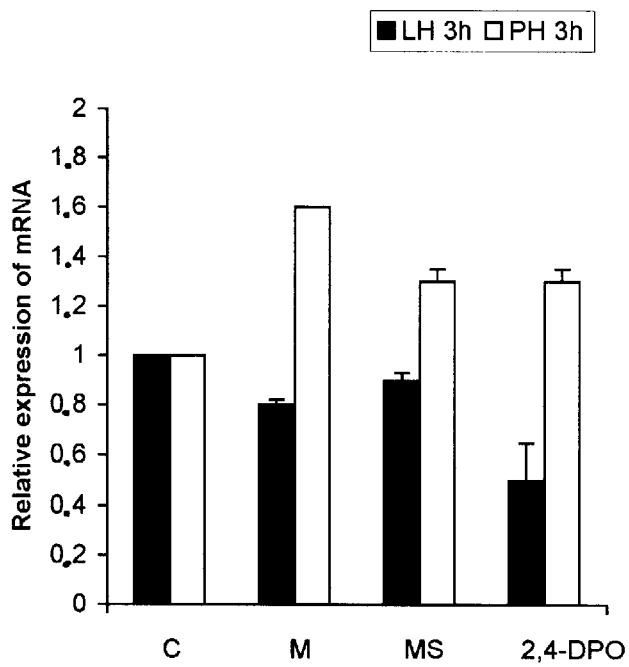
FIG. 1B demonstrates Relative Expression of mRNA, as in FIG. 1A, at 18 h.

The results are presented in FIGS. 1A and 1B.

Hence it is seen that the incubation of fibroblasts for 3 hours in the presence of minoxidil or of minoxidil sulphate reduces the level of relative expression of the mRNAs coding for lysyl hydroxylase, this level then being 0.75.

After 3 hours of incubation in the presence of 2,4-DPO, the level of relative expression of the mRNAs coding for lysyl hydroxylase is 0.55.

Hence 2,4-DPO inhibits the expression of mRNAs coding for lysyl hydroxylase more than minoxidil or the sulphated analogue thereof.

Similar results are observed after 18 hours of culture in the presence of the various inhibitors tested.

Moreover, after 3 hours of culture in the presence of minoxidil or of minoxidil sulphate, the level of relative expression of the mRNAs coding for prolyl hydroxylase increases, reaching 1.25 and 1.85, respectively.

After 3 hours of incubation in the presence of 2,4-DPO, the level of relative expression of the mRNAs coding for prolyl hydroxylase is also higher, this level then being of the order of 1.3.

After 18 hours of culture in the presence of minoxidil, of minoxidil sulphate or of 2,4-DPO, the levels of relative expression of the mRNAs coding for prolyl hydroxylase are 1.6, 1,3 and 1.15, respectively.

Hence no inhibition of the level of relative expression of the mRNAs coding for prolyl hydroxylase in response to these three compounds is observed.

Hence the compounds tested display a specific inhibitory activity with respect to lysyl hydroxylase.

II—Study of the effect of 2,4-DPO on the collagen network present in the extracellular matrix of fibroblasts in culture 10 μM 2,4-DPO is added to a primary culture of human dermal fibroblasts, originating from material obtained in a mammaplasty, in DMEM medium supplemented with 10% of foetal calf serum.

After three days, the cells are lysed by hypoosmotic shock and the collagen deposit is fixed with 5% glutaraldehyde solution.

The extracellular matrix of the fibroblasts is then observed using a scanning electron microscope.

The extracellular matrix of a primary culture of untreated fibroblasts is also observed by scanning electron microscopy.

The extracellular matrix of untreated fibroblasts exhibits large fibrous clumps surrounding broad areas devoid of collagen network, while the extracellular matrix of the fibroblasts treated with 2,4-DPO exhibits a much more regular organization in which large fibrous clumps are not observed and where the size of the areas devoid of collagen network is far smaller.

The application of 2,4-DPO to a fibroblast culture hence brings about a spatial reorganization of the collagen fibres into a micro-network.

EXAMPLES OF THERAPEUTIC COMPOSITIONS

Example 1

Skin cream

A skin cream is prepared by mixing the following ingredients:

| | |
|---|---|
| 2,4-DPO | 0.5 g |
| Ceteareth 30 | 7 g |
| Glyceryl stearate | 2 g |
| Cetyl alcohol | 1.5 g |
| Polydimethylsiloxane | 1.5 g |
| Liquid paraffin | 15 g |
| Glycerol codex, pure | 20 g |
| Preservatives q.s. | |
| Demineralized water q.s. | 100 g |

Example 2

Skin lotion to be sprayed

A skin lotion to be sprayed is prepared by mixing the following ingredients:

| | |
|---|---|
| 2,4-DPO | 0.25 g |
| Ethanol | 30 g |
| Demineralized water q.s. | 100 g |

Example 3

Injection

A solution for intradermal injection is prepared by mixing the following ingredients:

| | |
|---|---|
| 2,4-DPO | 0.7 mg |
| Physiological saline (9 g NaCl/H$_2$O q.s. 100 ml) q.s. | 1 ml |

We claim:

1. Process for the treatment of collagen maturation and structuring disorders comprising administering to a subject a therapeutic composition which is in a form which can be administered topically, transdermally or intradermally, said composition containing an effective amount of 2,4-diaminopyrimidine 3-oxide (2,4-DPO) or a physiologically acceptable salt thereof to treat said disorders.

2. The process according to claim 1 wherein said salt is selected from the group consisting of sulphuric, hydrochloric, phosphoric, acetic, benzoic, salicylic, glycolic, aceturic, succinic, nicotinic, tartaric, maleic, methanesulphonic, picric and lactic acids.

3. The process according to claim 1 wherein said composition is in a form which can be topically administered and the proportion of 2,4-DPO is between 0.0001 and 50% by weight relative to the total weight of the composition.

4. The process according to claim 3 wherein the proportion of 2,4-DPO is between 0.01 and 2% by weight relative to the total weight of the composition.

5. The process according to claim 1 wherein the composition is in a form which can be administered transdermally and the proportion of 2,4-DPO is between 0.001 and 5% by weight relative to the total weight of the composition.

6. The process according to claim 5 wherein the proportion of 2,4-DPO is between 0.01 and 2% by weight relative to the total weight of the composition.

7. The process according to claim 1 wherein said composition is in a form which can be administered intradermally and the proportion of 2,4-DPO is between 0.0001 and 5% by weight relative to the total weight of the composition.

8. The process according to claim 1 wherein the subject is a human.

9. The process according to claim 1 wherein the subject is an animal.

10. The process according to claim 9 wherein the animal is a member of the family Equidae.

11. The process according to claim 7 wherein the proportion of 2,4,-DPO is between 0.01 and 1% by weight relative to the total weight of the composition.

* * * * *